United States Patent [19]
Holla et al.

[11] Patent Number: 6,018,053
[45] Date of Patent: Jan. 25, 2000

[54] PROCESS FOR THE PREPARATION OF CHIRAL, NONRACEMIC (4-ARYL-2,5-DIOXOIMIDAZOLIDIN-1-YL) ACETIC ACIDS

[75] Inventors: Wolfgang Holla, Kriftel; Gerhard Beck; Bernhard Kammermeier, both of Frankfurt; Berndt Kulitzscher, Steinmark; Jürgen Michalowsky, Kelkheim, all of Germany

[73] Assignee: Hoechst Aktiengesellschaft, Frankfurt am Main, Germany

[21] Appl. No.: 08/879,289

[22] Filed: Jun. 19, 1997

[30] Foreign Application Priority Data

Jun. 20, 1996 [DE] Germany .................. 196 24 604

[51] Int. Cl.[7] .................. C07D 233/76; C07D 233/80; C07D 233/72; C07D 233/78
[52] U.S. Cl. .................. 548/319.5; 548/317.1
[58] Field of Search .................. 548/317.1, 319.5

[56] References Cited

U.S. PATENT DOCUMENTS

| | | | |
|---|---|---|---|
| 2,829,157 | 4/1958 | McKinney | 548/317.1 X |
| 3,939,175 | 2/1976 | Schmidt et al. | 548/317.1 |
| 5,436,256 | 7/1995 | Hendel et al. | 548/321.1 |
| 5,627,201 | 5/1997 | Gaillard-Kelly et al. | 514/386 |

FOREIGN PATENT DOCUMENTS

| | | |
|---|---|---|
| 0132854A2 | 2/1985 | European Pat. Off. |
| 0182279A1 | 5/1986 | European Pat. Off. |
| 0468592A2 | 1/1992 | European Pat. Off. |
| 0529835A2 | 3/1993 | European Pat. Off. |
| WO 95/14008 | 5/1995 | WIPO |
| WO 96/33976 | 10/1996 | WIPO |

OTHER PUBLICATIONS

N. Buckley et al., "A Reinvestigation of the Alkylation of 5–(ρ–Hydroxyphenyl)–5–Phenylhydantoin," Clinica Chimica Acta, vol. 62, pp. 73–78 (1975).

M. B. Winstead et al., "Substitution in the Hydantoin Ring. I. N–3–Aminomethyl Derivatives," and "Substitution in the Hydantoin Ring. II. N–3–Acetic Derivatives," Notes, vol. 8, pp. 117–122 (Jan. 1965).

H.U. Stilz et al., "From Peptides to Heterocyclic Peptide Mimetics—Design and Synthesis of an Orally Active Fibrinogen Receptor Antagonist for the Prevention of Thrombosis," Bull. Soc. Chim. Belg., vol. 105, No. 10–11, pp. 711–719 (1996).

J. Falbe et al., "Racemattrennung," Römpp Chemic Lexikon, vol. 9 No. 5, pp. 3753–3754 (1992).

Primary Examiner—Floyd D. Higel
Attorney, Agent, or Firm—Finnegan, Henderson, Farabow, Garrett & Dunner, L.L.P.

[57] ABSTRACT

The present invention relates to a process for the preparation of chiral, nonracemic compounds of the formula I

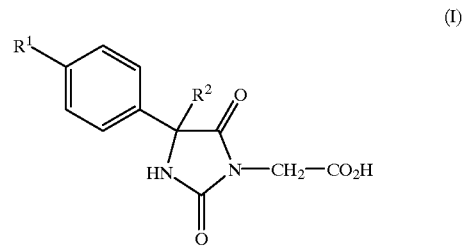

(I)

in which $R^1$ and $R^2$ have the meanings indicated in claim 1 and which are useful intermediates for the preparation of pharmaceutical active compounds in which, for resolution, a salt is formed from the racemic compound of the formula I and a chiral, nonracemic amino compound. It furthermore relates to compounds of the formula I and esters thereof.

19 Claims, No Drawings

PROCESS FOR THE PREPARATION OF CHIRAL, NONRACEMIC (4-ARYL-2,5-DIOXOIMIDAZOLIDIN-1-YL) ACETIC ACIDS

The present invention relates to a process for the preparation of chiral, nonracemic compounds of the formula I,

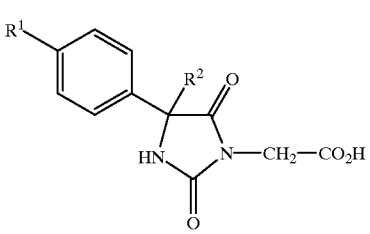

which are useful intermediates for the preparation of pharmaceutical active compounds in which, for resolution, a salt is formed from the racemic compound of the formula I and a chiral, nonracemic amino compound. It furthermore relates to compounds of the formula I and esters thereof.

The PCT application PCT/EP 94/03491 describes hydantoin derivatives which inhibit cell-cell adhesion, in particular, for example, platelet aggregation. Inter alia, compounds are disclosed therein which contain a (4-aryl-2,5-dioxoimidazolidin-1-yl)acetyl unit. The pharmacological activity of these substances depends, inter alia, on the configuration at C-4 of the 2,5-dioxoimidazolidine or hydantoin ring. The preparation of active compounds with uniform configuration at C-4 of the hydantoin ring takes place laboriously according to PCT application PCT/EP94/03491 by carrying out at the active compound stage a chromatographic resolution of a stereoisomer mixture which, with respect to C-4 of the hydantoin ring, is a mixture of the R-form and the S-form.

The German patent application 195 15 177 and the PCT application PCT/EP96/01572 describe hydantoin derivatives, among them also hydantoinacetic acids of the forumla I, which can be employed as intermediates in the synthesis of the active compounds described in the PCT application PCT/EP94/03491. Enantiomerically pure hydantoinacetic acids, which are suitable for the preparation of active compounds with uniform configuration at C-4 of the hydantoin ring, are only obtainable according to PCT application PCT/EP96/01572 by laborious processes in multistage syntheses, for example by reacting a carbonyl compound in a Bucherer reaction to give a hydantoin, hydrolyzing this to the amino acid, esterifying the amino acid, carrying out a resolution with the amino acid ester, reacting the enantiomerically pure compound with an ester of isocyanatoacetic acid and finally cyclizing the resulting product under acidic conditions to give the hydantoinacetic acid.

These known methods for the preparation of the active compounds with uniform configuration at C-4 of the hydantoin ring described in the PCT application PCT/EP94/03491 are unacceptable, because of their low total yield and the laborious process, for active compound production on an industrial scale. There is therefore a need for a simple synthetic method for the preparation of the desired active compounds.

Surprisingly, it has been found that nonracemic hydantoinacetic acids of the formula I can be prepared simply and in high optical and chemical yields by resolution at the stage of the conveniently accessible racemic compounds of the forumla I, in which a salt is formed from the racemic compound of the formula I and a chiral, nonracemic amino compound. Using the nonracemic hydantoinacetic acids of the formula I thereby obtainable, in which the R-configuration or the S-configuration is thus uniformly or predominantly present at C-4, the desired active compounds can then be prepared according to the details in the PCT application PCT/EP96/01572. The racemic compounds of the formula I employed in the resolution, i.e. the enantiomer mixtures, can be prepared according to or analogously to known methods, thus, for example, also according to the details in the PCT application PCT/EP94/03491.

The present invention thus relates to a process for the preparation of chiral, nonracemic compounds of the formula I

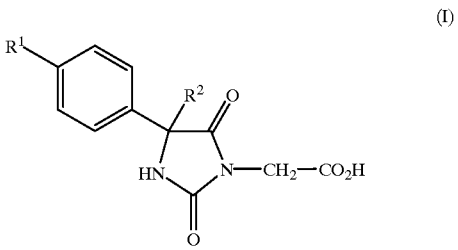

in which
R$^1$ is hydrogen, fluorine, chlorine, bromine, iodine, cyano, nitro or hydroxyl, and
R$^2$ is hydrogen, fluorine, (C$_1$–C$_7$)-alkyl, phenyl-(C$_1$–C$_7$)-alkyl or (C$_3$–C$_8$)-cycloalkyl,
which comprises carrying out a resolution with the racemic compound of the formula I, in which a salt is formed from the racemic compound of the formula I and a chiral, nonracemic amino compound.

Alkyl radicals can be straight-chain or branched. This also applies if they are substituted. Examples of alkyl radicals are methyl, ethyl, n-propyl, isopropyl, n-butyl, isobutyl, sec-butyl, tert-butyl, n-pentyl, isopentyl, neopentyl, n-hexyl, isohexyl, n-heptyl. Preferred alkyl radicals are methyl, ethyl, n-propyl, isopropyl and tert-butyl, particularly preferably methyl and ethyl.

In phenyl-(C$_1$–C$_7$)-alkyl radicals, the phenyl group can be located in any desired position in the alkyl group. Examples of phenyl-(C$_1$–C$_7$)-alkyl radicals are benzyl, 1-phenylethyl, 2-phenylethyl, 3-phenylpropyl, 4-phenylbutyl and 6-phenylhexyl. Preferred radicals are phenyl-(C$_1$–C$_4$)-alkyl radicals, a particularly preferred radical is benzyl.

Examples of cycloalkyl radicals are cyclopropyl, cyclobutyl, cyclopentyl, cyclohexyl, cycloheptyl and cyclooctyl. Cycloalkyl radicals can also be substituted by one or more alkyl radicals, in particular methyl radicals. A preferred cycloalkyl radical is the cyclopropyl radical.

R$^1$ is preferably chlorine, bromine, iodine, cyano or hydroxyl, particularly preferably chlorine, bromine or cyano.

R$^2$ is preferably hydrogen, fluorine, (C$_1$–C$_4$)-alkyl, in particular methyl or ethyl, phenyl-(C$_1$–C$_4$)-alkyl, in particular benzyl, or (C$_3$–C$_7$)-cycloalkyl, in particular cyclopropyl, particularly preferably hydrogen, methyl or ethyl, very particularly preferably methyl or ethyl, additionally preferably methyl.

It is furthermore preferred if, simultaneously, R$^1$ is chlorine, bromine or cyano and R$^2$ is methyl or ethyl.

As used herein, the term "stereoisomers" is a general term for all isomers of individual molecules that differ only in the orientation of their atoms is space. It includes enantiomers and isomers of compounds with more than one chiral center that are not mirror images of one another (diastereomers). The term "chiral center" refers to a carbon atom to which four different groups are attached. The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction. The term "racemic" refers to a mixture of equal parts of enantiomers and which is optically inactive. As used herein the prefixes "(+)" and "(−)" are employed to designate the sign of rotation of plane polarized light by the compound, with (+) meaning the compound is dextrorotatory and (−) meaning the compound is levorotatory. The term "resolution" refers to the separation or concentration or depletion of one of the two enantiomeric forms of a molecule. The term "fractional crystallization" refers to a procedure in which in and/or after salt formation a crystallization of one of the two diastereomeric salts or of a salt mixture in which one of the two salts predominates takes place.

The present application deals with enantiomeric enrichment which refers to the increase in the amount of one enantiomer as compared to its corresponding opposite enantiomer. A convenient method of expressing enantiomeric enrichment achieved is the concept of "enantiomeric excess" or "ee", which is expressed by the following equation;

$$ee = \frac{E^1 - E^2}{E^1 + E^2} \times 100$$

in which $E^1$ is the amount of the first enantiomer and $E^2$ is the amount of the second corresponding enantiomer. For example, where the initial ratio of two enantiomers in a reaction is 50:50 (a racemic mixture) and the reaction produces enantiomeric enrichment with a final ratio of 90:10, then the ee with respect to the first enantiomer of the final product is 80%.

The preparation of the racemic compounds of the formula I employed in the resolution can be carried out by methods familiar to the person skilled in the art. For example, the starting material used can be a carbonyl compound of the formula II

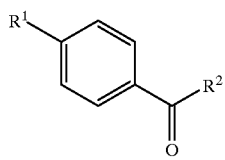

(II)

in which
  $R^1$ is hydrogen, fluorine, chlorine, bromine, iodine, cyano, nitro or hydroxyl and
  $R^2$ is hydrogen, $(C_1-C_7)$-alkyl, phenyl-$(C_1-C_7)$-alkyl or $(C_3-C_8)$-cycloalkyl.

Preferably, the starting materials used are carbonyl compounds of the formula II, in which $R^1$ is hydrogen, cyano, bromine, chlorine, iodine or hydroxyl, particularly preferably bromine or hydroxyl. Preferred meanings of $R^2$ in the formula II are hydrogen, $(C_1-C_4)$-alkyl, in particular methyl and ethyl, phenyl-$(C_1-C_4)$-alkyl, in particular benzyl, and $(C_3-C_7)$-cycloalkyl, in particular cyclopropyl, particularly preferred meanings of $R^2$ in the formula II are methyl and ethyl.

The compounds of the formula II can be converted under the known conditions of the Bucherer reaction (H. T. Bucherer, V. A. Lieb, J. Prakt. Chem. 141 (1934), 5–43), by reaction with potassium cyanide and ammonium carbonate, into the racemic hydantoins of the formula III,

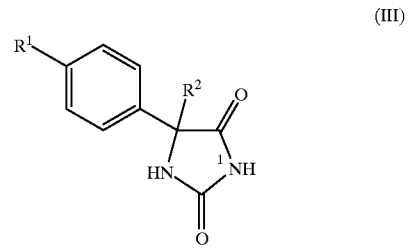

(III)

in which $R^1$ and $R^2$ are defined as indicated for the formula II. The compounds of the formula III can be alkylated analogously to methods known from the literature (see, for example, Houben-Weyl, Methoden der Organischen Chemie [Methods of Organic Chemistry], Volume XI/1, p. 81 et seq., or M. Orena et al., J. Org. Chem. 57 (1992), 6532) in the presence of bases, for example alkoxides or alkali metal hydroxides or carbonates such as potassium hydroxide or potassium carbonate, using haloacetic acid esters of the formula IV

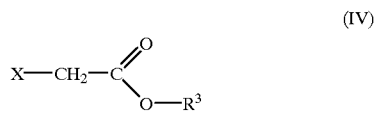

(IV)

in which X is chlorine, bromine or iodine, in particular chlorine or bromine, and $R^3$, for example, is $(C_1-C_6)$-alkyl, in particular methyl, ethyl or tert-butyl, or benzyl, on N-1 to give the esters of the formula V

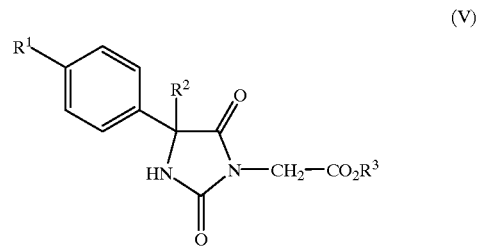

(V)

in which $R^1$ and $R^2$ are defined as indicated for the formula III and $R^3$ is defined as indicated for the formula IV. A particularly preferred compound of the formula IV is methyl chloroacetate. It is also possible in the alkylation to add catalytic substances, e.g. iodides such as potassium iodide or sodium iodide, when using chloro- or bromoacetic acid esters. The esters of the formula V can then be converted by methods familiar to the person skilled in the art, e.g. using aqueous mineral acids such as hydrochloric acid or aqueous alkali hydroxide solutions such as sodium hydroxide solution, into the racemic hydantoinacetic acids of the formula I. The conversion of the esters of the formula V into the acids can be carried out directly following the alkylation without isolation of the ester, but the esters can also be isolated in between.

Compounds of the formula I in which $R^2$ is fluorine can be prepared from compounds in which $R^2$ is hydrogen according to customary fluorination methods known to the person skilled in the art (see, for example, Nachr. Chem. Tech. Lab. 38 (1990), 40).

In the racemic compounds of the forumla I, it is also possible, if desired, to carry out a conversion of the substituent $R^1$. Thus, for example, compounds of the formula I in which $R^1$ is halogen can be converted by a halogen-cyanide exchange carried out analogously to known processes, e.g. by a bromine-cyanide exchange, into compounds of the formula I in which $R^1$ is cyano (N. Chatani and T. Hanafusa, J. Org. Chem. 51 (1986), 4714; J. R. Dalton and S. L. Regen, J. Org. Chem. 44 (1979), 4443), and compounds in which $R^1$ is hydroxyl can be converted, directly or after conversion of the hydroxyl group into, for example, the methylsulfonyloxy group or the trifluoromethylsulfonyloxy group, by a cyanide exchange into compounds in which $R^1$ is cyano (M. R. I. Chambers and D. A. Widdowson, J. Chem. Soc. Perkin Trans. I (1989), 1365; V. Percec et al., J. Org. Chem 60 (1995), 6895; and literature cited therein), and compounds in which $R^1$ is hydrogen can be converted directly into compounds in which $R^1$ is cyano (G. Lohaus, Chem. Ber. 100 (1967), 2719). Such conversions can also be carried out in the nonracemic compounds of the formula I.

The salt formation of the racemic compound of the formula I and the chiral, nonracemic amino compound to be carried out for resolution is carried out according to the customary procedure by combination of the two components in a solvent, diluent or dispersant. The subsequent actual resolution is then carried out utilizing the different properties which the salt of the R-form of the compound of the formula I and the chiral, nonracemic amino compound has on the one hand and the salt of the S-form of the compound of the formula I and the chiral, nonracemic amino compound has on the other hand. When combining the two components, the racemic compound of the formula I can be initially introduced and the amino compound can be metered in or conversely, and also both components can be metered into the reaction vessel simultaneously.

As chiral, nonracemic amino compounds for the resolution, amines can be employed which beside amino groups contain no further functional groups in the molecule, as well as amines which also contain one or more further functional groups, e.g. hydroxyl groups, ether groups, carboxyl groups, carboxylate groups, ester groups or amide groups. The amino compounds can be saturated or unsaturated and can also contain aromatic radicals, in particular unsubstituted or substituted phenyl radicals. They can contain primary, secondary and tertiary amino groups, and amino groups can also be part of a ring system. Preferably, amines, aminoalcohols, amino acids and amino acid derivatives, particularly preferably aminoalcohols, are employed. Examples of suitable chiral amino compounds are (+)-phenylalanine, (−)-phenylalanine, (+)-ephedrine, (−)-ephedrine, (+)-norephedrine, (−)-norephedrine, (+)-phenylalaninol, (−)-phenylalaninol, (R)-phenylalanine methyl ester, (S)-phenylalanine methyl ester or (L)-N-methylglucosamine.

The choice of the solvent, diluent or dispersant, in the following collectively described as solvent, in which the racemic compound of the formula I and the chiral, nonracemic amino compound are combined for salt formation, depends on the individual case, i.e. on the particular combination of amino compound and compound of the formula I and the properties of their salts as well as on the intended procedure for the resolution. Suitable solvents are, for example, water and organic solvents such as alcohols, e.g. methanol, ethanol, propanol and isopropanol, ethers, e.g. tert-butyl methyl ether, dioxane, tetrahydrofuran and mono- and dimethyl ethers of ethylene glycol and of diethylene glycol, ketones, e.g. acetone and butanone, esters, e.g. ethyl acetate and tert-butyl acetate, and hydrocarbons and halogenated hydrocarbons, e.g. toluene and methylene chloride. Mixtures of two or more solvents can also be employed, for example mixtures of water and ethanol, of water and methanol, of isopropanol and tert-butyl methyl ether or of water and ethyl acetate, e.g. in the form of water-saturated ethyl acetate. Frequently, it is expedient to work in an aqueous-organic solvent, i.e. in a mixture of water and one or more organic solvents, or in water.

The racemic compound of the formula I and the chiral, nonracemic amino compound can be combined for salt formation in the molar ratio 1:1, but one of the two components can also be employed in an excess or in a substoichiometric amount. Preferably, 0.5 to 1 mol of amino compound are employed relative to 1 mol of racemic compound of the formula I. If the amino compound is employed in a substoichiometric amount, it can be advantageous to add a nonchiral auxiliary base which completely or partially neutralizes the part of the compound of the formula I not converted into the salt by the amino compound. In this case, preferably up to 0.5 mol of auxiliary base are employed relative to 1 mol of racemic compound of the formula I. Suitable auxiliary bases are, for example, alkali metal hydroxides, such as lithium, sodium or potassium hydroxide.

Salt formation is in general carried out at temperatures from −15° C. to 100° C., preferably 0° C. to 80° C.

In the separation or concentration or depletion of one of the two enantiomeric forms of the compound of the formula I from the original racemic mixture which is to be carried out after salt formation to cleave the racemate, the fact can be utilized that the formation of one of the two diastereomeric salts, i.e. of the salt of the R-form of the compound of the formula I and of the chiral, nonracemic amino compound on the one hand and of the salt of the S-form of the compound of the formula I and of the chiral, nonracemic amino compound on the other hand, takes place preferably and/or that solubility differences exist between these two salts. Only one of the two salts, for example, may precipitate from the solvent employed or one of the two salts may precipitate to a greater extent than the other. The precipitated salt can then be isolated, for example, by filtering or centrifuging, and this salt and/or the mother liquor can be further processed. For the separation or concentration or depletion of one form, however, it is also possible, for example, to carry out a distribution between two nonmiscible liquid phases or an extraction. Preferably, a fractional crystallization is used. For preparation of a specific enantiomer of the forumla I, it may also be advantageous here to select the conditions such that it is not the desired but rather the undesired enantiomer that precipitates as a salt with the chiral amino compound, and the desired enantiomer initially remains in the mother liquor.

In the preferred procedure using fractional crystallization, the reaction mixture from salt formation preferably contains 2.5 to 40 per cent by weight, particularly preferably 10 to 30 per cent by weight, of racemic compound of the forumla I, based on the total weight of the reaction mixture. The temperature during the crystallization process is in general −15° C. to 100° C., preferably 0° C. to 80° C. It can be changed during the crystallization, for example the crystallization can first be initiated at a relatively high temperature and the temperature can then be lowered. Frequently, it is favorable to establish a temperature of −5° C. to 30° C. at the end.

The salt precipitating in the fractional crystallization or the mother liquor often already contains one or the other enantiomeric form of the compound of the formula I in a high optical purity which suffices for active compound synthesis. If the enantiomer contained in the precipitating salt is desired in a higher purity, it is possible after isolation of this salt, e.g. by filtering or centrifuging, for a further concentration, e.g. by recrystallization, to follow. This recrystallization, which is a further fractional crystallization, can be carried out once or several times until the optical purity desired in the individual case is achieved. The above details for the solvents in salt formation apply correspondingly to the solvents which can be employed in the recrystallization of the salts of the compounds of the formula I and the chiral, nonracemic amino compounds. Preferably, water, alcohols such as methanol, ethanol or isopropanol, or mixtures of these, e.g. mixtures of water and ethanol, are employed in the recrystallization.

In the recrystallization, the concentration of the salt employed is preferably 2.5 to 40 per cent by weight, particularly preferably 10 to 30 per cent by weight, based on the total weight of the recrystallization mixture. The temperature during recrystallization is in general −15° C. to 100° C., preferably 0° C. to 80° C. Frequently, it is favorable to establish a temperature of −5° C. to 30° C. at the end before the isolation of the precipitated crystals, e.g. by filtration or centrifugation.

If the enantiomer which is contained in the form of its salt with the chiral amino compound in the mother liquor of the crystallization which has taken place after salt formation is desired in a higher optical purity than that initially achieved, it is possible, for example, to concentrate the mother liquor partially or completely and to recrystallize the resulting salt according to the above details.

To release the enantiomerically pure compounds of the formula I with the desired optical purity from their salts with the chiral amino compounds, the salts isolated directly after salt formation or after recrystallization can be dissolved or suspended by the customary procedure, e.g. in water or in an organic solvent or in a mixture of water and an organic solvent and treated with a strong acid, e.g. with a mineral acid such as hydrochloric acid, nitric acid, phosphoric acid or sulfuric acid, in particular with an aqueous mineral acid. The resulting free carboxylic acids of the formula I can then be isolated, for example, by filtration, centrifugation, phase separation or extraction, depending on the conditions in the individual case. Preferably, the release of the carboxylic acids of the formula I is carried out in water or a mixture of water and an organic solvent, e.g. in a water/ethyl acetate mixture, a pH of about 0 to 2 is established using aqueous mineral acid and the carboxylic acid is isolated by phase separation and/or extraction, e.g. with ethyl acetate, and subsequent concentration of the organic phase and drying of the residue. Analogously, i.e., for example, by acidification and extraction, to the described release from the isolated salts, also the carboxylic acids of the formula I can be obtained which are left in the mother liquor of a crystallized salt during salt formation. This applies both to carboxylic acids which are left in the mother liquor in the form of their salts with the chiral amino compounds and to salts with optionally added auxiliary bases.

The chiral, nonracemic amino compound used for the resolution can be recovered from the acidic solution remaining in the release of the compounds of the formula I after their isolation. For this, a procedure can be used in which the acidic solution is adjusted to a pH of 11 or greater using a strong base, e.g. an alkali metal hydroxide such as sodium hydroxide solution or potassium hydroxide solution, and the amino compound then present in the form of the free base is isolated, e.g. by extraction from an aqueous solution or suspension using an organic solvent such as ethyl acetate, drying and concentration of the extracts. Before use in a resolution again, the recovered amino compound can also be purified, e.g. by digesting with a solvent or by recrystallization.

According to the process of the present invention chiral, nonracemic compounds of the formula I which have very good optical purities and are therefore outstandingly suitable for the preparation of the desired pharmaceutical active compounds having uniform configuration at C-4 of the hydantoin ring, are obtained in high chemical yields and in a simple manner which can be carried out easily on an industrial scale. Further processing to give pharmaceutical active compounds can be carried out, for example, according to the processes described in the PCT applications PCT/EP94/03491 and PCT/EP96/01572, the disclosure of which is herein incorporated by reference, for the racemic and the nonracemic compounds of the formula I.

The present invention furthermore relates to compounds of the formula I as such, which in racemic form are the starting substances for the process according to the invention described above or which are obtained in nonracemic form when carrying out this process, and which are useful intermediates for the preparation of pharmaceutical active compounds. The nonracemic compounds of the formula I can in this case be present in the form of pure enantiomers or in the form of mixtures of the enantiomers in any desired ratios (the racemic compound being present at a ratio of 1:1). In particular, the present invention relates to compounds of the formula Ia

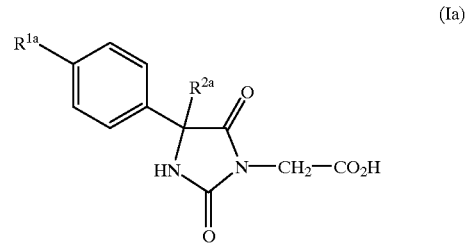

(Ia)

in which $R^{1a}$ is fluorine, chlorine, bromine or hydroxyl and $R^{2a}$ is $(C_1-C_4)$-alkyl or benzyl, in racemic or nonracemic form, the compound of the formula Ia present in the form of the pure enantiomers being excluded in which $R^{1a}$ is bromine and $R^{2a}$ is methyl.

The above explanations for the process according to the invention and for the compounds of the formula I apply to the compounds of the formula Ia correspondingly. Examples of the $(C_1-C_4)$-alkyl group representing $R^{2a}$ in the formula Ia are methyl, ethyl, n-propyl, isopropyl, n-butyl, isobutyl, sec-butyl and tert-butyl. Preferably, $R^{2a}$ is methyl or ethyl, particularly preferably methyl. Compounds of the formula Ia in which $R^{1a}$ is bromine are a subject of the present invention, especially in racemic form. A preferred compound which, as such, is a subject of the present invention is the compound of the formula Ia in which $R^{1a}$ is bromine and $R^{2a}$ is methyl, in racemic form, i.e. the compound of the formula Ib

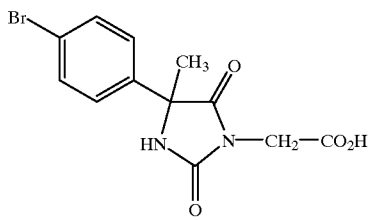

(Ib)

in racemic form, which can be employed as a starting material in the process according to the invention described above.

The preparation of the compounds of the formula Ia and the compound of the formula Ib can be carried out, for example, by reacting the corresponding racemic hydantoins of the formula III with haloacetic acid esters of the formula IV as explained above to give the racemic compounds of the formula Va

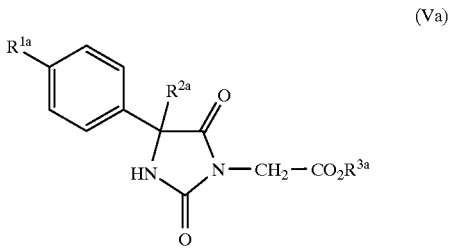

(Va)

in which
$R^{1a}$ is fluorine, chlorine, bromine or hydroxyl,
$R^{2a}$ is $(C_1-C_4)$-alkyl or benzyl and
$R^{3a}$, for example, is $(C_1-C_6)$-alkyl or benzyl,
and hydrolyzing these racemic esters as described above, for example using aqueous mineral acids or alkali metal hydroxide solutions, to give the acids of the to formula Ia or to give the acid of the formula Ib in racemic form, from which the acids of the formula Ia or the acid of the formula Ib in nonracemic form are then obtainable by the process according to the invention. The compounds of the formula Va in racemic form are also a subject of the present invention. For these also, the above explanations apply correspondingly. Preferably, $R^{1a}$ and $R^{2a}$ in the formula Va have the preferred meanings indicated for the formula Ia. $R^{3a}$ in the formula Va is preferably $(C_1-C_4)$-alkyl, in particular methyl, ethyl or tert-butyl, or benzyl. Preferred compounds are those compounds of the formula Va in racemic form in which $R^{1a}$ is bromine, $R^{2a}$ is methyl and $R^{3a}$ is $(C_1-C_4)$-alkyl, in particular methyl or ethyl, i.e. the racemic compounds of the formula Vb

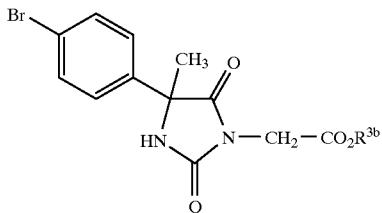

(Vb)

in which $R^{3b}$ is $(C_1-C_4)$-alkyl, in particular methyl or ethyl. The compounds of the formulae Va and Vb are also useful intermediates for pharmaceutical active compounds. The compounds of the formulae Va and Vb can be isolated as explained above after their preparation from the compounds of the formulae III and IV, but they can likewise also be hydrolyzed directly without isolation to the acids of the formula Ia or to the acid of the formula Ib. If the hydrolysis is carried out under alkaline conditions, salts of these acids are first formed, which of course are likewise comprised by the present invention.

EXAMPLES

The products are identified by their $^1$H-NMR spectra and mass spectra. The enantiomeric excess (ee) of an acid of the formula I in the (R)-form or the (S)-form in the products obtained was determined by high-pressure liquid chromatography (HPLC) (column: S,S-Whelk-01 (250 mm×4 mm) from E. Merck, Darmstadt: detector, UV 240/254 mm; eluent: n-hexane+ethanol+glacial acetic acid (90+10+1 parts by volume); flow rate: 1 ml/min; temperature: 40° C.). The salts obtained in the examples were investigated directly by HPLC. The determination of the absolute configuration of the compounds of the formula I was carried out by means of the independent preparation of the nonracemic compounds from the corresponding optically pure amino acids known from the literature (cf. PCT application PCT/EP96/01572).

Example 1

(R,S)-4-Phenyl-4-methyl-2,5-dioxoimidazolidine 21.0 g of acetophenone, 15.8 g of potassium cyanide and 54.0 g of ammonium carbonate are heated at 110° C. in an autoclave for 8 h at 10 bar in 340 ml of water-ethanol (1:1). The mixture is then diluted with 500 ml of water and 90 ml of conc. hydrochloric acid are added cautiously with ice-cooling (heavy foaming, formation of hydrogen cyanide). The precipitated product is filtered off, washed with water and dried. Yield: 29.1 g (87.5%) of the racemic title compound. M.p. 194 to 195° C.

Example 2

(R,S)-4-(4-Bromophenyl)-4-methyl-2,5-dioxoimidazolidine 29.4 ml of ethanol and 29.4 ml of water are initially introduced into an autoclave and mixed successively with 5.8 g of 4-bromoacetophenone, 2.48 g of potassium cyanide and 8.4 g of ammonium carbonate. The reaction mixture is heated at 110° C. for 8 h at 8 to 9 bar. After cooling to room temperature, it is diluted with 30 ml of water and adjusted to a pH of 3 to 4 by cautious addition of about 27 ml of half-conc. hydrochloric acid. The resulting white precipitate is filtered off, washed with a little water and dried at 50° C. in a drying oven. Yield: 7.7 g (98%) of the racemic title compound. M.p. 275° C.

Example 3

(R,S)-4-(4-Cyanophenyl)-4-methyl-2,5-dioxoimidazolidine 65.0 g of 4-cyanoacetophenone, 43.2 g of potassium cyanide and 132.0 g of ammonium carbonate are heated at 110° C. for 8 h at 10 bar (nitrogen) in 700 ml of water-ethanol (1:1) in an autoclave. The mixture is then diluted with 350 ml of water and acidified cautiously with about 460 ml of half-conc. hydrochloric acid to a pH of 3.5. The precipitated product is filtered off, washed with water and dried. Yield: 58 g (61%) of the racemic title compound. M.p. 206° C.

Example 4
(R,S)-(4-(4-Bromophenyl)-4-methyl-2,5-dioxoimidazolidin-1-yl)acetic acid 10.58 g of (R,S)-4-(4-bromophenyl)-4-methyl-2,5-dioxoimidazolidine are initially introduced into 25 ml of N-methylpyrrolidone at room temperature and treated with 5.87 g of ground potassium carbonate and 5.45 g of methyl chloroacetate. The reaction mixture is heated at 50° C. for 2 h, then cooled to 25° C. and diluted with 250 ml of water. By addition of 8 to 9 ml of conc. sodium hydroxide solution, a pH of 11 is established, then the mixture is stirred for 30 min at room temperature and for a further 30 min at 40 to 50° C. The clear colorless solution obtained is cooled to 25° C., acidified to a pH of 1 to 1.5 using 13 to 15 ml of conc. hydrochloric acid and additionally stirred at 15 to 20° C. for a further 60 min. The precipitated crystalline product is filtered off, washed with a little water until neutral and dried at 60° C. in vacuo. Yield: 10.5 g (83%) of the racemic title compound. M.p. 240 to 241° C.

Example 5
(R,S)-(4-(4-Bromophenyl)-4-methyl-2,5-dioxoimidazolidin-1-yl)acetic acid 10.0 g of (R,S)-4-(4-bromophenyl)-4-methyl-2,5-dioxoimidazolidine are initially introduced into 50 ml of N-methylpyrrolidone at room temperature and treated with 4.74 g of potassium tert-butoxide and 4.7 ml of ethyl bromoacetate. The reaction mixture is heated at 120° C. for 2.5 h, then cooled to 25° C. and added to 200 ml of water. After saturating with sodium chloride, it is extracted with a total of 100 ml of ethyl acetate. The combined organic phases are concentrated and the residue is heated to 90 to 100° C. with 50 ml of conc. hydrochloric acid. The crystallized product is filtered off, washed with water and dried in vacuo. Yield: 9.5 g (79%) of the racemic title compound. M.p. 239 to 241° C.

Example 6
(R,S)-(4-(4-Cyanophenyl)-4-methyl-2,5-dioxoimidazolidin-1-yl)acetic acid 34.4 g of (R,S)-4-(4-cyanophenyl)-4-methyl-2,5-dioxoimidazolidine are initially introduced into 80 ml of N-methylpyrrolidone at room temperature and treated with 24.32 g of ground potassium carbonate and 16.32 ml of methyl chloroacetate. The reaction mixture is stirred at 50 to 60° C. for 2 h, then cooled to 25° C. and diluted with 800 ml of water. A pH of 11 is established with conc. sodium hydroxide solution, then the mixture is stirred at room temperature for 30 min and at 40 to 50° C. for a further 30 min. After cooling to 25° C., it is acidified to a pH of 1 using 344 ml of 2 N hydrochloric acid and extracted three times with about 250 ml of ethyl acetate. The combined organic phases are washed with saturated sodium chloride solution, dried with sodium sulfate and concentrated in vacuo. 51.2 g of an oil are obtained, which is crystallized from diisopropyl ether. Yield: 36.3 g (83%) of the racemic title compound. M.p. 227 to 229° C.

Example 7
(R,S)-(4-(4-Cyanophenyl)-4-methyl-2,5-dioxoimidazolidin-1-yl)acetic acid 12.5 g of (R,S)-(4-(4-bromophenyl)-4-methyl-2,5-dioxoimidazolidin-1-yl)acetic acid and 15.4 g of copper(I) cyanide are heated at 155° C. for 8 h in 65 ml of dimethylformamide, then the mixture is allowed to cool to about 25° C. overnight with stirring. The greenish solution obtained from the initially white suspension is treated with 195 ml of water, and the pH is adjusted from 3 to pH=1 to 1.5 using conc. hydrochloric acid. The mixture is stirred for 30 min, 8 g of Celite® filter aid and 50 g of sodium chloride are added, and it is stirred for a further 15 min and filtered. The aqueous phase is extracted three times using 40 ml of ethyl acetate each time. The combined organic phases are washed three times with 25 ml of saturated sodium chloride solution each time. The sodium chloride solutions are discarded. The organic phase is treated with 100 ml of dilute sodium hydroxide solution and the mixture is filtered through a Seitz filter layer. The organic phase is separated off and discarded, and the alkaline aqueous phase is acidified to a pH of 1 to 1.5 using concentrated hydrochloric acid. The product which initially precipitates in oily form crystallizes after a short time. It is additionally stirred at 10° C. for 1 h, and the product is filtered off, washed with water until neutral and dried. Yield: 7.5 g (72%) of the racemic title compound. M.p. 224 to 226° C.

Example 8
(S)-(4-(4-Bromophenyl)-4-methyl-2,5-dioxoimidazolidin-1-yl)acetic acid 10.8 g of (R,S)-(4-(4-bromophenyl)-4-methyl-2,5-dioxoimidazolidin-1-yl)acetic acid and 5.0 g of (R)-phenylalaninol are stirred at 80° C. for 15 min in 90 ml of isopropanol. The mixture is cooled to 20 to 25° C., the crystallized product is filtered off and 10.3 g of the (R)-phenylalaninol salt are obtained, which is recrystallized from 110 ml of ethanol. After stirring at 5° C. for 2 hours, the crystallized product is filtered off and dried. Yield: 4.4 g of the (R)-phenylalaninol salt of the title acid.

To release the free acid, the salt is suspended in 44 ml of water, acidified with dilute hydrochloric acid to a pH of 1, and the resulting precipitate is filtered off, digested with water and dried. Yield: 2.85 g of the title acid with 66% ee of the (S)-form (HPLC).

$[\alpha]^{20}_D$=+18° (c=1; 2.15 N ethanolic hydrogen chloride solution).

Example 9
(R)-Phenylalaninol salt of (S)-(4-(4-cyanophenyl)-4-methyl-2,5-dioxoimidazolidin-1-yl)acetic acid 30.0 g of (R,S)-(4-(4-cyanophenyl)-4-methyl-2,5-dioxoimidazolidin-1-yl)acetic acid are dissolved in 600 ml of ethanol at 40° C. and treated with 9.96 g of (R)-phenylalaninol. The mixture is stirred at 0 to 5° C. for 16 h and the precipitated product is filtered off.

Yield: 14.8 g of the title salt with 82% ee of the (S)-acid (HPLC). M.p. 185–187° C.

Example 10
(R)-Phenylalaninol salt of (S)-(4-(4-cyanophenyl)-4-methyl-2,5-dioxo-imidazolidin-1-yl)acetic acid 3.8 g of the salt obtained according to Example 9 are dissolved in 105 ml of ethanol at boiling heat. The mixture is allowed to cool and is stirred at 0 to 5° C. for 1.5 h, and the precipitated product is filtered off and dried. Yield: 3.0 g of the title salt with 97.5% ee of the (S)-acid (HPLC). M.p. 193 to 195° C.

Example 11
(S)-Phenylalaninol salt of (R)-(4-(4-cyanophenyl)-4-methyl-2,5-dioxoimidazolidin-1-yl)acetic acid 25 g of (R,S)-(4-(4-cyanophenyl)-4-methyl-2,5-dioxoimidazolidin-1-yl)acetic acid are treated with 13.8 g of (S)-phenylalaninol at 20 to 25° C. in a mixture of 150 ml of isopropanol and 150 ml of tert-butyl methyl ether. After stirring overnight, the precipitated product is filtered off and dried. Yield: 9.3 g of the title salt with 71.3% ee of the (R)-acid (HPLC). By recrystallizing twice from isopropanol/ acetone, the title salt with 99.4% ee of the (R)-acid is obtained in a yield of 3 g.

Example 12
(R)-Phenylalaninol salt of (S)-(4-(4-cyanophenyl)-4-methyl-2,5-dioxoimidazolidin-1-yl)acetic acid 27.3 g of (R,S)-(4-(4-cyanophenyl)-4-methyl-2,5-dioxoimidazolidin-1-yl)acetic acid are added at 20° C. to 15.1 g of (R)-phenylalaninol in 150 ml of water with stirring. The mixture is stirred at 20° C. for 10 min, then at 60° C. for 1 h, a clear solution being formed. The mixture is then cooled to 20° C. in the course of 3 h and additionally stirred at this temperature for 15 h. The precipitated product is filtered off with suction, washed with 20 ml of water and 40 ml of acetone and dried. Yield: 18.9 g of the title salt with 89.8% ee of the (S)-acid (HPLC). M.p. 191 to 194° C.

Example 13
(R)-Phenylalaninol salt of (S)-4-(4-cyanophenyl)-4-methyl-2,5-dioxoimidazolidin-1-yl)acetic acid 18.9 g of the salt obtained in Example 12 are stirred at 60° C. for 1 h in 65 ml of water. The suspension is cooled to 20° C. in 3 h and additionally stirred at this temperature for 15 h. The precipitated product is filtered off with suction, washed with 10 ml of water and dried at 40° C. in vacuo. Yield: 15.7 g of the title salt with 99.4% ee of the (S)-acid (HPLC). M.p. 199° C.

$[\alpha]^{20}_D = -18°$ (c=1; methanol)

Example 14
(S)-(4-(4-Cyanophenyl)-4-methyl-2,5-dioxoimidazolidin-1-yl)acetic acid 12.9 g of the (R)-phenylalaninol salt of (S)-(4-(4-cyanophenyl)-4-methyl-2,5-dioxoimidazolidin-1-yl)acetic acid obtained according to Example 13 are initially introduced into a mixture of 60 ml of water and 50 ml of ethyl acetate. By addition of half-conc. hydrochloric acid, a pH of 1 is established. The aqueous phase is separated off and is used for the recovery of (R)-phenylalaninol. The organic phase is washed with water and concentrated in vacuo. The residue is treated with 10 ml of toluene and the mixture is evaporated to dryness.

Yield: 8.2 g of the title acid with 99.4% ee of the (S)-form (HPLC). $[\alpha]^{20}_D = +56°$ (c=1; 29.2% strength ethanolic hydrogen chloride solution).

Example 15
Recovery of (R)-phenylalaninol

The aqueous phase obtained according to Example 14 and containing the (R)-phenylalaninol is adjusted to a pH of 11 using conc. sodium hydroxide solution and extracted 4 times with 10 to 20 ml of ethyl acetate each time. The combined organic phases are dried with magnesium sulfate and evaporated in vacuo. The residue is digested with tert-butyl methyl ether and filtered off with suction.

Yield: 3.8 g of (R)-phenylalaninol. M.p. 92 to 93° C. $[\alpha]^{20}_D = +25.5°$ (c=1.2; 1 N aqueous hydrogen chloride solution).

Example 16
(S)-Phenylalaninol salt of (R)-(4-(4-cyanophenyl)-4-methyl-2,5-dioxo-imidazolidin-1-yl)acetic acid 19.6 g of (R,S)-(4-(4-cyanophenyl)-4-methyl-2,5-dioxoimidazolidin-1-yl)-acetic acid are heated to 60° C. in 90 ml of water and treated successively with 5.44 g of (S)-phenylalaninol, 2 g of potassium hydroxide and 20 ml of methanol. The mixture is stirred at 60° C. for 15 min, then cooled to 0° C. and stirred for 15 min at this temperature. The precipitated product is filtered off with suction and dried. Yield: 13.5 g of the title salt with 68.6% ee of the (R)-acid (HPLC). Recrystallization analogously to Example 13 affords 12.2 g of the title salt with 100% ee of the (R)-acid (HPLC). M.p. 199 to 200° C.

Example 17
(S)-Phenylalaninol salt of (R)-(4-(4-cyanophenyl)-4-methyl-2,5-dioxo-imidazolidin-1-yl)acetic acid 19.6 g of (R,S)-(4-(4-cyanophenyl)-4-methyl-2,5-dioxoimidazolidin-1-yl)-acetic acid are heated to 60° C. in 90 ml of water and treated successively with 5.44 g of (S)-phenylalaninol, 2 g of potassium hydroxide and 10 ml of ethanol. The mixture is stirred at 60 to 65° C. for 15 min, then cooled slowly to 0° C. and stirred at this temperature for 60 min. The precipitated product is filtered off and dried. Yield: 13.4 g of the title salt with 72.2% ee of the (R)-acid (HPLC). Recrystallization analogously to Example 13 affords 12.5 g of the title salt with 93.95% ee of the acid (HPLC). M.p. 199 to 200° C.

Example 18
(R)-Phenylalaninol salt of (S)-(4-(4-cyanophenyl)-4-methyl-2,5-dioxo-imidazolidin-1-yl)acetic acid 15.0 g of (R,S)-(4-(4-cyanophenyl)-4-methyl-2,5-dioxoimidazolidin-1-yl)-acetic acid in 300 ml of ethyl acetate and 11 ml of water are treated with 5.0 g of (R)-phenylalaninol at 40° C. The mixture is allowed to cool slowly and is stirred overnight at 0° C. The precipitated product is filtered off and dried. Yield: 10.0 g of the title salt with 88.3% ee of the (S)-acid (HPLC).

Example 19
(R)-Phenylalaninol salt of (S)-(4-(4-cyanophenyl)-4-methyl-2,5-dioxo-imidazolidin-1-yl)acetic acid The product obtained according to Example 18 is recrystallized twice from boiling isopropanol, the mixture first being slowly allowed to cool to 20 to 25° C. with stirring and then allowed to stand overnight at 5° C. The precipitated product is filtered off and dried. Yield: 8.4 g of the title salt with 99.5% ee of the (S)-acid (HPLC).

Example 20
(S)-Phenylalaninol salt of (R)-(4-(4-cyanophenyl)-4-methyl-2,5-dioxo-imidazolidin-1-yl)acetic acid 19.6 g of (R,S)-(4-(4-cyanophenyl)-4-methyl-2,5-dioxoimidazolidin-1-yl)-acetic acid are heated to 60° C. in 70 ml of water and treated with 2 g of potassium hydroxide, 5.44 g of (S)-phenylalaninol and 30 ml of ethanol. The mixture is stirred at 60° C. for 15 min, then cooled slowly to 20 to 25° C., stirred at this temperature for 16 h and then cooled to 0° C. The precipitated product is filtered off and dried in vacuo at 50° C.

Yield: 12.4 g of the title salt with 86.7% ee of the (R)-acid (HPLC). M.p. 196 to 197° C.

By stirring the salt thus obtained in 26 ml of water at 60 to 65° C. for 45 minutes, cooling to about 22° C., stirring overnight, filtering off the precipitated product and drying, 11.4 g of the title salt with 98.5% ee of the (R)-acid (HPLC) are obtained. M.p. 199 to 200° C.

Example 21
(S)-Phenylalaninol salt of (R)-(4-(4-cyanophenyl)-4-methyl-2,5-dioxo-imidazolidin-1-yl)acetic acid 19.6 g of (R,S)-(4-(4-cyanophenyl)-4-methyl-2,5-dioxoimidazolidin-1-yl)-acetic acid, 5.44 g of (S)-phenylalaninol and 2 g of potassium hydroxide are heated to 60° C. in 105 ml of water, then cooled slowly to 20 to 25° C. and stirred at this temperature for 1 h. The precipitated product is filtered off and dried. Yield: 10.8 g of the title salt with 94.4% ee of the (R)-acid (HPLC). M.p. 199 to 201° C.

Example 22
(+)-(1S,2R)-Ephedrine salt of (S)-(4-(4-cyanophenyl)-4-methyl-2,5-dioxo-imidazolidin-1-yl)acetic acid 7.1 g of (R,S)-(4-(4-cyanophenyl)-4-methyl-2,5-dioxoimidazolidin-1-yl)-acetic acid are heated to about 45° C. in 40 ml of acetone and treated with 2.13 g of (+)-(1S, 2R)-ephedrine. The mixture is then slowly cooled to 20 to 25° C. The precipitated product is filtered off and dried. Yield: 5.4 g of the title salt with 35% ee of the (S)-acid (HPLC).

Example 23
(+)-(1S,2R)-Ephedrine salt of (S)-(4-(4-cyanophenyl)-4-methyl-2,5-dioxo-imidazolidin-1-yl)acetic acid The product obtained according to Example 22 is dissolved in 40 ml of ethanol with heating and then cooled to 20 to 250° C. The precipitated product is filtered off and dried. Yield: 2.7 g of the title salt with 98.1% ee of the (S)-acid (HPLC).

Example 24
(+)-(1S,2R)-Ephedrine salt of (R,S)-(4-(4-cyanophenyl)-4-methyl-2,5-dioxoimidazolidin-1-yl)acetic acid 7.1 g of (R,S)-(4-(4-cyanophenyl)-4-methyl-2,5-dioxoimidazolidin-1-yl)acetic acid are treated in 200 ml of methylene chloride with 2.13 g of (+)-(1S,2R)-ephedrine and stirred at 20 to 25° C. for 4 h. The precipitated product is filtered off and dried. Yield: 8.8 g of the title salt with ≦1% ee of the acid (HPLC).

Example 25
(+)-(1S,2R)-Ephedrine salt of (S)-(4-(4-cyanophenyl)-4-methyl-2,5-dioxo-imidazolidin-1-yl)acetic acid The product obtained according to Example 24 is dissolved in 40 ml of ethanol with heating and the solution is then cooled to 20 to 25° C. The precipitated product is filtered off and dried. Yield: 3.6 g of the title salt with 94.8% ee of the (S)-acid (HPLC).

Example 26
(S)-(4-(4-Cyanophenyl)-4-methyl-2,5-dioxoimidazolidin-1-yl)acetic acid 3 g of the (+)-(1S,2R)-ephedrine salt of (S)-(4-(4-cyanophenyl)-4-methyl-2,5-dioxoimidazolidin-1-yl)acetic acid obtained according to Example 23 are initially introduced into a mixture of 15 ml of water and 15 ml of ethyl acetate. By addition of half-conc. hydrochloric acid, a pH of 1 is established. The aqueous phase is separated off and can be used for the recovery of the (+)-(1S,2R)-ephedrine analogously to Example 15. The organic phase is washed with water and concentrated in vacuo. The residue is treated twice with toluene and the mixture evaporated to dryness. Yield: 1.82 g of the title acid with 98% ee of the (S)-form (HPLC).

Example 27
(+)-(1S,2R)-Ephedrine salt of (S)-(4-(4-bromophenyl)-4-methyl-2,5-dioxo-imidazolidin-1-yl)acetic acid 6.5 g of (R,S)-(4-(4-bromophenyl)-4-methyl-2,5-dioxoimidazolidin-1-yl)-acetic acid and 1.98 g of (+)-(1S, 2R)-ephedrine are heated to reflux in 240 ml of ethanol. The mixture is first slowly allowed to cool to 20 to 25° C. and then stirred at 0 to 4° C. for a further 2 h. The precipitated product is filtered off and dried. Yield: 2.3 g of the title salt with 70% ee of the (S)-acid (HPLC).

What is claimed is:

1. A process for the preparation of chiral, nonracemic compounds of the formula

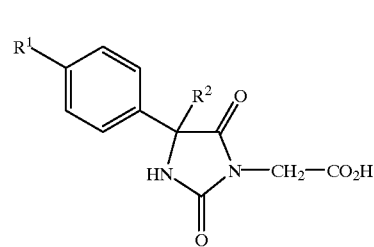

(I)

wherein $R^1$ is hydrogen, fluorine, chlorine, bromine, iodine, cyano, nitro or hydroxyl and $R^2$ is hydrogen, fluorine, $(C_1-C_7)$-alkyl, phenyl-$(C_1-C_7)$-alkyl or $(C_3-C_8)$-cycloalkyl, comprising carrying out a resolution by separating, concentrating or depleting one of the two enantiomeric forms of the racemic compound of the forumla I, by forming a salt from the racemic compound of the formula I and a chiral nonracemic amino compound.

2. The process according to claim 1, wherein $R^1$ is chlorine, bromine, iodine, cyano or hydroxyl.

3. The process according to claim 1, wherein $R^2$ is hydrogen, fluorine, $(C_1-C_4)$-alkyl, benzyl or $(C_3-C_7)$-cycloalkyl, preferably hydrogen, methyl or ethyl.

4. The process according to claim 1 wherein said racemic compound of formula I is prepared according to a process comprising reacting a carbonyl compound of the formula II

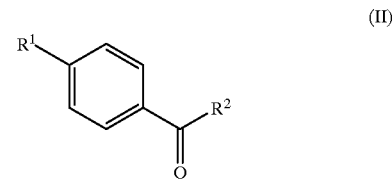

(II)

wherein $R^1$ is hydrogen, fluorine, chlorine, bromine, iodine, cyano, nitro or hydroxyl and $R^2$ is hydrogen, $(C_1-C_7)$-alkyl, phenyl-$(C_1-C_7)$-alkyl or $(C_3-C_8)$-cycloalkyl, under the conditions of the Bucherer reaction to give a hydantoin of the formula III

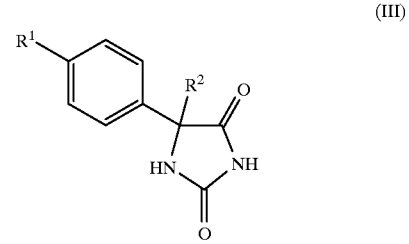

(III)

wherein $R^1$ and $R^2$ are defined as indicated for the formula II, alkylating said hydantoin of formula II using a haloacetic acid ester of the formula IV

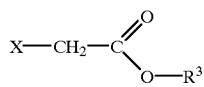

(IV)

wherein X is chlorine, bromine or iodine and $R^3$ is $(C_1–C_6)$-alkyl or benzyl, to give a compound of the formula V

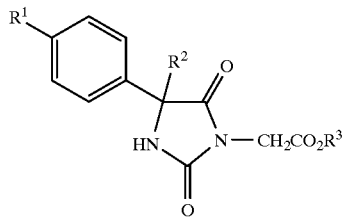

(V)

wherein $R^1$ and $R^2$ are defined as indicated for the formula II and $R^3$ is $(C_1–C_6)$-alkyl or benzyl, and hydrolyzing said ester of the formula V into the acid of the formula I.

5. The process according to claim 1, wherein the chiral, nonracemic amino compound is from the group consisting of amines, aminoalcohols, amino acids or amino acid esters.

6. The process according to claim 5, wherein the chiral, nonracemic amino compound is an aminoalcohol.

7. The process according to claim 1 which further comprises adding a nonchiral auxiliary base during salt formation.

8. The process according to claim 1 wherein said salt is formed in water, aqueous-organic solvents or alcohols.

9. The process according to claim 8 wherein said alcohol is from the group consisting of methanol, ethanol and isopropanol.

10. The process according to claim 1 wherein said salt is fractionally crystallized.

11. The process according to claim 1 wherein said salt is fractionally crystallized, isolated, and recrystallized.

12. The process according to claim 1 which further comprises treating the salt formed from the racemic compound of the formula I and the chiral, nonracemic amino compound with a mineral acid to yield the chiral, nonracemic compound of the formula I.

13. The process according to claim 1 wherein the chiral, nonracemic compound of the formula I is (S)-(4-(4-cyanophenyl)-4-methyl-2,5-dioxoimidazolidin-1-yl)acetic acid.

14. The process according to claim 1 wherein the chiral, nonracemic compound of the formula I is (S)-(4-(4-bromophenyl)-4-methyl-2,5-dioxoimidazolidin-1-yl)acetic acid.

15. A compound of the formula Ia

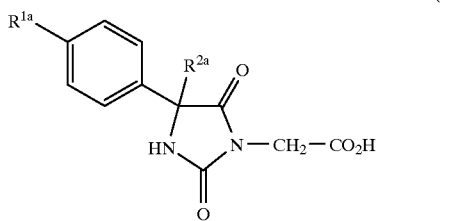

(Ia)

wherein $R^{1a}$ is fluorine, chlorine, bromine or hydroxyl and $R^{2a}$ is $(C_1–C_4)$-alkyl or benzyl, in racemic or nonracemic form, with the proviso that the compound of the formula Ia is not in the form of a pure enantiomer when $R^{1a}$ is bromine and $R^{2a}$ is methyl.

16. A compound according to claim 15 wherein $R^{1a}$ is bromine and $R^{2a}$ is methyl, in racemic form.

17. A compound of the formula Va

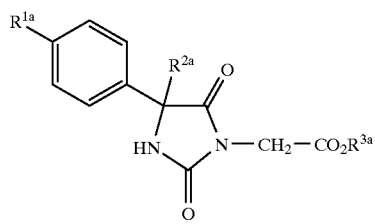

(Va)

wherein $R^{1a}$ is fluorine, chlorine, bromine or hydroxyl, $R^{2a}$ is $(C_1–C_4)$-alkyl or benzyl and $R^{3a}$ is $(C_1–C_6)$-alkyl or benzyl, in racemic form.

18. A compound of the formula Va according to claim 17 wherein $R^{1a}$ is bromine, $R^{2a}$ is methyl and $R^{3a}$ is $(C_1–C_4)$-alkyl, in racemic form.

19. The process according to claim 3, wherein $R^2$ is hydrogen, methyl, or ethyl.

* * * * *